US006080549A

United States Patent [19]

Deth

[11] Patent Number: 6,080,549
[45] Date of Patent: Jun. 27, 2000

[54] METHODS AND MATERIALS FOR THE DIAGNOSIS AND TREATMENT OF SCHIZOPHRENIA AND RELATED DISORDERS

[75] Inventor: Richard C. Deth, Waban, Mass.

[73] Assignee: Northeastern University, Boston, Mass.

[21] Appl. No.: 08/833,703

[22] Filed: Apr. 8, 1997

[51] Int. Cl.$^7$ .................. G01N 33/567; G01N 33/48
[52] U.S. Cl. .................. 435/7.21; 435/15; 436/63; 436/501; 436/504; 436/505; 436/804; 436/811
[58] Field of Search .................. 435/7.2, 7.21, 435/40.51; 436/501, 504, 71, 63, 804, 811

[56] References Cited

FOREIGN PATENT DOCUMENTS

| WO9005780 | 5/1990 | European Pat. Off. . |
| WO9606856 | 3/1996 | European Pat. Off. . |
| WO9637780 | 11/1996 | European Pat. Off. . |

OTHER PUBLICATIONS

Deth et al., FASEB Journal, 10(3):A283, Mar. 8, 1996.

Baldessarini et al., "Methylation in Schizophrenia: An Old Hypothesis Revisited," pp. 127–140 (1978).

Chou et al., "The Enzymatic Synthesis of Adenosylmethionine: Mechanism and Inhibition," *The Biochemistry of Adenosylmethionine*, (NY: Columbia University Press), pp. 18–36 (1977).

Coligan et al., (John Wiley & Sons, Inc.), "Antibody Detection and Preparation," *Current Protocols in Immunology, National Institutes of Health*, pp. 2.0.1–2.5.17 (1994).

De La Rosa et al., "Changes in the Relative Amount of Subunits of Methionine Adenosyltransferase in Human Lymphocytes upon Stimulation with a Polyclonal T cell Mitogen," *J. Biol. Chem.*, vol. 267(15): pp 10699–10704.

Hibert et al., "Three–Dimensional Models of Neurotransmitter G–Binding Protein–Coupled Receptors," *Molecular Pharmacology*, vol. 40: pp 8–15 (1991).

Hilf et al., "Activation of Cardiac G–Proteins by Muscarinic Acetylcholine Receptors: Regulation by $Mg^{2+}$ and $Na^+$ ions," *European J. Pharmacology*, vol. 172: pp 155–163 (1989).

Hirata et al., "Phospholipid Methylation and Biological Signal Transmission," *Science*, vol. 209: pp 1082–1090 (1980).

Hoffman et al., "Fractionation of Methionine Adenosyltransferase Isozymes (Rat Liver)," *Methods in Enzymology*, vol. 94: pp 223–247 (1983).

Ismail et al., "Altered Metabolism of the Methionine Methyl Group in the Leukocytes of Patients with Schizophrenia," *Society of Biological Psychiatry* pp. 649–660 (1978).

Israelstam et al., "Abnormal Methionine Metabolism in Schizophrenic and Depressive States: a Preliminary Report," *J. Psychiat. Res.*, vol. 7: pp. 185–190 (1970).

Iversen, L. L., "The D4 and Schizophrenia," *Nature*, vol. 365: p. 393 (1993).

Kelsoe et al., "Kinetic Evidence for Decreased Methionine Adenosyltransferase Activity in Erythrocytes from Schizophrenics," *J. Neuroscience Research*, vol. 8: pp 99–103 (1982).

Kemali et al., "Antidepressant Effects of Adenosyl–Methionine: Clinical and Methodological Issues Emerging from Preliminary Trials," *Biochemical and Pharmacological Roles of Adenosylmethionine and the Central Nervous System*, Zappia et al., eds. (NY: Pergamon Press), pp. 141–147 (1978).

Le Fur et al., "Evidence for a Coupling Between Dopaminergic Receptors and Phospholipid Methylation in Mouse B Lymphocytes," *Life Sciences*, vol. 29: pp 2737–2749 (1981).

Macciardi et al., "Analysis of the $D_4$ Dopamine Receptor Gene Variant in an Italian Schizophrenia Kindred," *Arch. Gen. Psychiatry*, vol. 51: pp 288–294 (1994).

Mezey et al., "Localization of Targets for Anti–Ulcer Drugs in Cells of the Immune System," *Science*, vol. 258: pp 1662–1665 (1992).

O'Dowd, B.F., "Structures of Dopamine Receptors," *J. Neurochemistry*, vol. 60(3): pp 804–816 (1993).

Samama et al., "A mutation–Induced Activated State of the $\beta_2$–Adrenergic Receptor," *J. Biol. Chem.*, vol. 268 (7): pp. 4625–4636 (1993).

Sargent et al., "Tracer Kinetic Evidence for Abnormal Methyl Metabolism in Schizophrenia," *Biol. Psychiatry*, vol. 32: pp. 1078–1090 (1992).

Seeman et al., "Dopamine receptor pharmacology," *Trends Pharmacol. Sci.* vol. 15: pp. 264–270 (1994).

Seeman et al., "Brain Receptors for Antipsychotic Drugs and Dopamine: Direct Binding Assays," *Proc. Nat. Acad. Sci. USA*, vol. 72(11): pp. 4376–4380 (1975).

Seeman et al., "Dopamine Receptor Pharamcology," *Tips Receptor and Ion Channel Nomenclature Supplement*, S. Watson and D. Girdlestone, eds., 5th edition (1994).

Seeman et al., "Dopamine D4 Receptors Elevated in Schizophrenia," *Nature*, vol. 365: pp 441–445 (1993).

Smythies et al., "Abnormalities of One–Carbon Metabolism in Psychiatric Disorders: Study of Methionine Adenosyltransferase kinetics and Lipid Composition of Erythrocyte Membranes," *Biol. Psychiatry*, vol. 21: pp. 1391–1398 (1986).

Szymanski et al., "A Selective Review of Biological Markers in Schizophrenia," *Schizophrenia Bulletin*, vol. 17(1): pp. 99–111 (1991).

Taubes, G., "Will Dopamine Receptors Offer a Key to Schizophrenia?" *Science*, vol. 265: pp 1034–1035 (1994).

(List continued on next page.)

*Primary Examiner*—Patricia A. Duffy
*Attorney, Agent, or Firm*—Weingarten, Schurgin, Gagnebin & Hayes LLP

[57] ABSTRACT

Methods for detecting schizophrenia or depression based on modifications of the contribution of the $D_4$ receptor to phospholipid methylation levels are described herein. Individuals with schizophrenia or depression have a deficiency in phospholipid methylation activity compared with normal individuals. Methods for screening therapeutic processes or agents for use in treatment of schizophrenia or related neuropsychiatric disorders are also described.

4 Claims, 4 Drawing Sheets

OTHER PUBLICATIONS

Teeter et al., "Homology Modeling of the Dopamine $D_2$ Receptor and Its Testing by Docking of Agonists and Tricyclic Antagonists," *J. Med. Chem.*, vol. 37(18): pp. 2874–2888 (1994).

Tolbert et al., "Defects in Transmethylation and Membrane Lipids in Schizophrenia," *Psychopharmacology Bulletin*, vol. 19(4): 594–599 (1983).

Trolin et al., "Brain ATP:L–Methionine S–Adenosyltransferase (MAT), S–Adenosylmethionine (SAM) and S–Adenosylhomocysteine (SAH): Regional Distribution and Age–Related Changes," *European Neuropsychopharmacology*, vol. 4: pp. 469–477 (1994).

Van Tol et al., "Cloning of the Gene for a Human Dopamine $D_4$ Receptor With High Affinity for the Antipsychotic Clozapine," *Nature*: vol. 350: pp. 610–614 (1991).

"Schizophrenia and Other Psychotic Disorders," *Diagnostic and Statistical Manual of Mental Disorders*, (Washington, D.C.: American Psychiatric Association) Fourth Edition, pp. 273–296.

Deth et al., "Lymphocyte Phospholipid Methylation is altered in Schizophrenia," *Biol. Psychiatry*, vol. 39: p 504, Abstract only (1996).

Deth et al., "Kinase–Dependent Spontaneous Activity of G Protein–Coupled Receptors," *Biol. Psychiatry*, vol. 39: p 581, Abstract only (1996).

Deth et al., "Adensoylation of the Dopamine $D_4$ Receptor Causes Spontaneous Activity," *Biol. Psychiatry*, vol. 39: p 631, Abstract only (1996).

Deth et al., "Methyl Donation by $D_4$ Dopamine receptors in phospholipid methylation," *Biol. Psychiatry*, vol. 39: p 504, Abstract only (1996).

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 387 amino acids
        (B) TYPE: amino acid
        (C) STRANDEDNESS: single
        (D) TOPOLOGY: linear     (xi) SEQUENCE DESCRIPTION: SEQ ID NO:1:

```
Met Gly Asn Arg Ser Thr Ala Asp Ala Asp Gly Leu Leu Ala Gly Arg
 1               5                  10                  15

Gly Pro Ala Ala Gly Ala Ser Ala Gly Ala Ser Ala Gly Leu Ala Gly
                20                  25                  30

Gln Gly Ala Ala Ala Leu Val Gly Gly Val Leu Leu Ile Gly Ala Val
             35                  40                  45

Leu Ala Gly Asn Ser Leu Val Cys Val Ser Val Ala Thr Glu Arg Ala
         50                  55                  60

Leu Gln Thr Pro Thr Asn Ser Phe Ile Val Ser Leu Ala Ala Ala Asp
 65                  70                  75                  80

Leu Leu Leu Ala Leu Leu Val Leu Pro Leu Phe Val Tyr Ser Glu Val
                85                  90                  95

Gln Gly Gly Ala Trp Leu Leu Ser Pro Arg Leu Cys Asp Ala Leu Met
            100                 105                 110

Ala Met Asp Val Ala Leu Cys Thr Ala Ser Ile Phe Asn Leu Cys Ala
            115                 120                 125

Ile Ser Val Asp Arg Phe Val Ala Val Ala Val Pro Leu Arg Tyr Asn
        130                 135                 140

Arg Gln Gly Gly Ser Arg Arg Gln Leu Leu Leu Ile Gly Ala Thr Trp
145                 150                 155                 160

Leu Leu Ser Ala Ala Val Ala Ala Pro Val Leu Cys Gly Leu Asn Asp
                165                 170                 175

Val Arg Gly Arg Asp Pro Ala Val Cys Arg Leu Glu Asp Arg Asp Tyr
            180                 185                 190

Val Val Tyr Ser Ser Val Cys Ser Phe Leu Pro Cys Pro Leu Met
        195                 200                 205

Leu Leu Leu Tyr Trp Ala Thr Phe Arg Gly Leu Gln Arg Trp Glu Val
```

-continued

```
            210                 215                 220
Ala Arg Arg Ala Lys Leu His Gly Arg Ala Pro Arg Arg Pro Ser Gly
225                 230                 235                 240

Pro Gly Pro Pro Ser Pro Thr Pro Pro Ala Pro Arg Leu Pro Gln Asp
                245                 250                 255

Pro Cys Gly Pro Asp Cys Ala Pro Pro Ala Pro Gly Leu Pro Pro Asp
            260                 265                 270

Pro Cys Gly Ser Asn Cys Ala Pro Pro Asp Ala Val Arg Ala Ala Ala
            275                 280                 285

Leu Pro Pro Gln Thr Pro Pro Gln Thr Arg Arg Arg Arg Arg Ala Lys
    290                 295                 300

Ile Thr Gly Arg Glu Arg Lys Ala Met Arg Val Leu Pro Val Val Val
305                 310                 315                 320

Gly Ala Phe Leu Leu Cys Trp Thr Pro Phe Phe Val Val His Ile Thr
                325                 330                 335

Gln Ala Leu Cys Pro Ala Cys Ser Val Pro Pro Arg Leu Val Ser Ala
            340                 345                 350

Val Thr Trp Leu Gly Tyr Val Asn Ser Ala Leu Asn Pro Val Ile Tyr
            355                 360                 365

Thr Val Phe Asn Ala Glu Phe Arg Asn Val Phe Arg Lys Ala Leu Arg
    370                 375                 380

Ala Cys Cys
385
```

METHODS AND MATERIALS FOR THE DIAGNOSIS AND TREATMENT OF SCHIZOPHRENIA AND RELATED DISORDERS

BACKGROUND OF THE INVENTION

Schizophrenia is a devastating neuropsychiatric disorder which affects approximately 1% of the population and results in serious disruption in the lives of afflicted individuals and their families. Common symptoms include delusions, conceptual disorganizations and visual or auditory hallucinations, as well as changes in affective behavior. A number of scales for the rating of symptoms and methods for ascertaining the diagnosis have been developed, including the DSM classification by the American Psychiatric Association (Diagnostic and Statistical Manual of Mental Disorders (4th edition), pp. 273–316, 1994), which have attempted to refine the accuracy of clinical diagnosis. However, it is likely that similar symptoms can result from several underlying abnormalities, and diagnosis relying solely on clinical symptoms is difficult and controversial, as well as subjective, time-consuming and costly.

The cause or causes of schizophrenia remain obscure. A defect in dopamine pathways of synaptic neuronal function is a central feature of the most widely held etiopathogenic theory (known as the Dopamine Hypothesis), with recent emphasis on the role of $D_4$-type dopamine receptors (Taubes, Science 265:1034–1035, 1994). However, studies to date have failed to identify abnormalities in the basic receptor structure, suggesting that dysfunction may result from an alteration in the dynamic regulation of receptor activity.

Dopamine receptors are members of a large superfamily of G protein-coupled receptors which share a high degree of structural similarity while recognizing a widely divergent array of substances which affect cellular function. Recent advances in the study of these receptors have led to the identification of key locations on the receptors which can modulate their function and which therefore may be sites of malfunction in schizophrenia (Samama et al., J. Biol. Chem. 268:4625–4636, 1993). One such critical location or "hot spot" in the dopamine $D_4$ receptor is a methionine amino acid residue (Van Tol et al., Nature 350:610–614, 1991).

A number of clinical and metabolic studies have documented altered methionine metabolism in individuals with schizophrenia (Kelsoe et al., J. Neurosci. Res. 8:99–103, 1982; Ismail et al., Biol. Psych. 13:649–660, 1978; Sargent et al., Biol. Psych. 32:1078–1090, 1992). For example, the administration of methionine has been shown to elicit an acute psychotic reaction in persons with schizophrenia but lacks such an effect in normal individuals (Cohen et al., Biol. Psych. 8:209–225, 1974). Conversely, administration of S-adenosylmethionine has been shown to have antidepressant benefits (Kemali et al., Biochemical and Pharmacological Roles of Adenosylmethionine and the Central Nervous System, Pergamon Press, pp. 141–147, 1979).

Recently, these findings have been integrated upon the discovery that methionine residue #313 (human $D_4$ receptor numbering) of the dopamine $D_4$ receptor appears to be abnormally modified in schizophrenic individuals (Deth, "Compositions and Methods for Detection of Schizophrenia," WO 96/37780, the whole of which is hereby incorporated by reference herein). Methionine residue #313 is normally modified by the addition of an adenosyl group to its sulfur atom via the action of a methionine adenosyltransferase (MAT) enzyme; however, individuals with schizophrenia are known to be deficient in MAT activity (Carl et al., Biol. Psych. 13:773–776, 1978) and, thus, are expected to possess a lesser amount of the modified form of the dopamine $D_4$ receptor. This deficiency is evident in a variety of tissues, including brain tissue and blood cells, particularly white blood cells, and is central to the biochemical diagnosis of schizophrenia.

BRIEF SUMMARY OF THE INVENTION

This invention is based upon the discovery that a biochemical abnormality in phospholipid methylation associated with schizophrenia is linked to the abnormal modification of the dopamine $D_4$ receptor and the clinical manifestations of altered dopamine neurotransmission. This discovery provides novel and empirical approaches for the diagnosis and treatment of schizophrenia and other related disorders.

This invention pertains to novel biochemical methods for assisting in the diagnosis of schizophrenia and other neuropsychiatric disorders, including, but not limited to, schizoaffective disorders, depression and dementias. The method of the present invention is based on the fact that dopamine receptor function is abnormal in individuals with schizophrenia, and upon the discoveries, described herein, that the dopamine $D_4$ receptor is a direct participant in the methylation of membrane phospholipids and that phospholipid methylation is abnormally altered in schizophrenic individuals. Consequently, an altered membrane fluidity may play a significant role in producing the symptoms of schizophrenia.

In one embodiment of the present invention, the level of phospholipid methylation in a tissue sample, e.g., peripheral blood cells (such as lymphocytes), from an individual to be tested is measured, preferably using $[^{14}C]$ formic acid labelling or any similar method of labelling the methylfolate pool. Additionally, the level of contribution of the $D_4$ receptor to phospholipid methylation in the same sample is also determined. The measured levels are then compared with corresponding levels of the same indicators from a tissue sample of a normal individual; a lower level of phospholipid methylation activity in the tested individual compared with the normal individual is indicative of schizophrenia or a related neuropsychiatric disorder in the tested individual. A lower level of $D_4$ receptor contribution to phospholipid methylation activity in the tested individual compared with the normal individual is indicative of schizophrenia specifically in the tested individual. Alternatively, a $[^{3}H]$-methyl-methionine based method of phospholipid methylation activity determination is used, a more indirect assay.

This invention also pertains to novel methods for identifying therapeutic processes or agents for treatment of schizophrenia or related neuropsychiatric disorders using cultured cell lines transfected with the $D_4$ receptor gene. Processes or agents identified by the methods described herein can increase the amount of phospholipid methylation to the normal level.

Furthermore, this invention also pertains to novel methods for determining the effectiveness of therapeutic processes or agents for treatment of neuropsychiatric disorders, and in particular schizophrenia. In one embodiment of the invention, the effectiveness of a therapeutic process or agent can be assessed by making an initial determination of the level of phospholipid methylation in a lymphocyte sample from an individual to be tested, administering the process or agent to be assessed, and making a subsequent determination of the level of phospholipid methylation in the lymphocyte sample from the individual. The corresponding levels of phospholipid methylation can be compared; an increase in the level of phospholipid methylation (preferably a normalization of methylation levels) indicates that the process or agent is effective for treating schizophrenia.

In a particular embodiment, the determination of the levels of phospholipid methylation is carried out using [$^{14}$C] formic acid labelling of the methylfolate pool. Thus, the present invention has utility for the identification of agents and processes for use in the treatment of schizophrenia, and such agents, processes and drugs are also the subject of this invention.

Any tissues which display the schizophrenia-associated alterations in methionine metabolism are suitable for use in the methods of the present invention. Such tissues include brain tissue and red and white blood cells. Peripheral blood cells (especially lymphocytes) are particularly useful in the present invention because of their accessibility, allowing the methods of the present invention to be carried out on a blood sample from the individual, and because lymphocyte membranes contain the $D_4$ receptor.

BRIEF DESCRIPTION OF THE DRAWINGS

Other features and advantages of the invention will be apparent from the following description of the preferred embodiments thereof and from the claims, taken in conjunction with the accompanying drawings, in which:

DETAILED DESCRIPTION OF THE INVENTION

The "Dopamine Hypothesis" is the most widely held biochemical explanation for the etiology of schizophrenia and theorizes a defect in dopamine pathways of synaptic neuronal function, with recent emphasis on the role of $D_4$-type dopamine receptors. Dopamine receptors are members of the superfamily of G protein-coupled receptors. All G protein-coupled receptors share the basic structural motif of seven transmembrane-spanning helices, formed as the single polypeptide chain traverses the plasma membrane (O'Dowd, J. Neurochem 60:804–816, 1993). In the case of the dopamine receptor, the neurotransmitter dopamine diffuses into the central core of the receptor on the outer surface of the cell where critical amino acid residues provide specific recognition. The binding of dopamine and its recognition by the receptor cause an alteration in the conformation of the receptor, and this "active" conformation conveys the neurotransmitter signal to GTP-binding G proteins located on the inner surface of the cell membrane.

Five subtypes of dopamine receptors have been identified, designated as $D_1$, $D_2$, $D_3$, $D_4$ and $D_5$. Based upon functional and structural similarities, the $D_1$ and $D_5$ receptors form a $D_1$-like receptor group, and the $D_2$, $D_3$ and $D_4$ receptors comprise a $D_2$-like group. Among dopamine receptors, the $D_1$-like receptors primarily complex with and activate the G protein $G_s$, while the $D_2$-like receptors activate the $G_i$ and/or $G_O$ proteins. The potency of neuroleptic drugs in treating schizophrenia has been found to be closely correlated with their antagonism of the $D_2$-like receptors (Seeman et al., Proc. Nat. Acad. Sci. USA 72:4376–4380, 1975), and antagonism of the $D_4$ receptor subtype provides a better correlation than do the $D_2$ or $D_3$ subtypes, implicating the $D_4$ receptor as the most likely target of neuroleptic drugs (Seeman and Van Tol, Trends Pharmacol Sci. 15:264–270, 1994).

Generally, a receptor must be occupied by its agonist or partial agonist in order to attain its active conformation and convey the neurotransmitter signal. However, in a phenomenon known as "spontaneous receptor activity," it is possible for a receptor to maintain the active conformation even in the absence of agonist occupation, although the extent of this phenomenon appears to be dependent upon prior exposure of the cells to the appropriate agonist.

Without wishing to be bound by theory, the binding of the agonist apparently induces a conformational change in the receptor, causing it to become active. In this active state, a modifiable amino acid residue (a "hot spot") on the intracellular portion of the receptor, exactly 18 residues (5 helical turns) from the agonist binding site, becomes accessible to a native enzyme. This enzyme modifies the "hot spot" such that the modification (typically a phosphorylation in other spontaneously active receptors but adenosylation in the $D_4$ receptor) prevents the receptor from returning to the inactive conformation upon departure of the agonist. In fact, the receptor remains in the active conformation and continues to propagate the neurotransmitter signal, until the modification is removed by subsequent enzyme activity.

Figure 1:
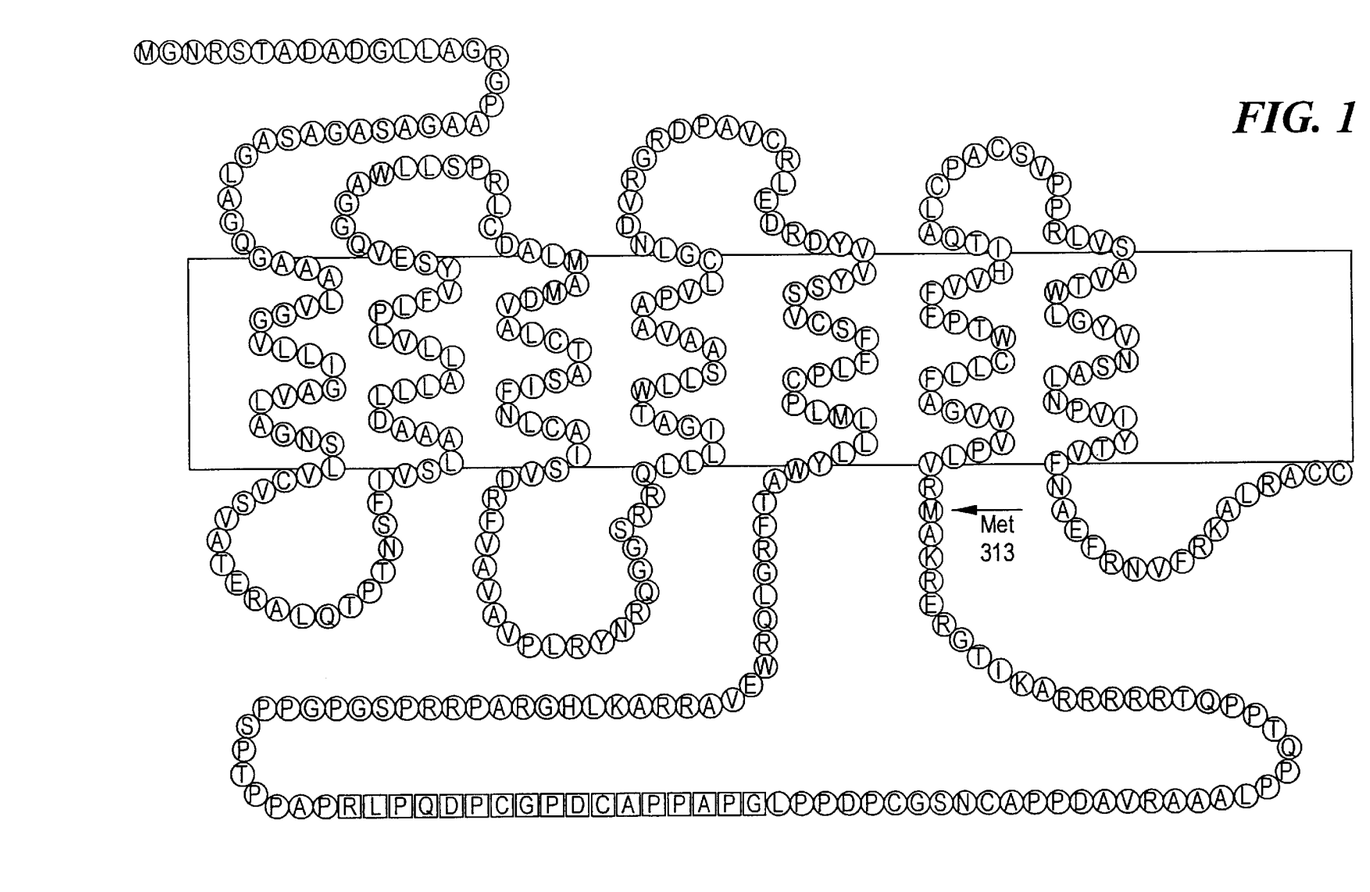
FIG. 1 is a prior art rendering of the dopamine $D_4$ receptor structure (SEQ ID NO:1), shown the amino acid sequence of the human dopamine $D_4$ receptor and its proposed seven transmembrane helical elements (Deth, WO 96/37780). The cell membrane is shown as a rectangle with the extracellular surface at the top and intracellular surface at the bottom. Methionine #313 (the "hot spot") is indicated with an arrow.

The dopamine $D_4$ receptor, methionine #313 (human $D_4$ receptor numbering) has been identified as such a "hot spot"; that is, referring to FIG. 1, methionine #313 is a modifiable amino acid residue on the intracellular portion of the $D_4$ receptor, located 18 residues (exactly 5 helical turns) below the key residue which is utilized by agonists to induce the active receptor conformation (Deth, "Compositions and Methods for Detecting Schizophrenia," WO 96/37780).

It has been shown that any modification of residues occupying the same position as dopamine $D_4$ receptor methionine #313 in other receptors will cause the receptor to become spontaneously active and exhibit spontaneous activity (Samama et al., J. Bio. Chem. 268:4625–4636, 1993). Similarly, it is believed that the binding of dopamine to the $D_4$ receptor causes an alteration of the receptor conformation to the active conformation. As a result of this alteration, methionine #313 becomes accessible to MAT, and MAT adds an adenosyl group to the sulfur atom of the methionine. This modification of methionine #313 by MAT prevents the re-configuration of the receptor to the inactive form upon departure of the agonist. Thus, the dopamine $D_4$ receptor is capable of spontaneously maintaining its active conformation, i.e., maintaining its active conformation without dopamine occupation. This active conformation is maintained until the modification (e.g., the adenosyl group) is removed by subsequent enzyme activity.

While phosphorylated threonine residues can be restored to their native state by the action of phosphatase enzymes, the fate of S-adenosylated methionine residue #313 was not immediately obvious. However, by analogy to S-adenosylmethionine, it was considered that the terminal methyl group may be available for donation in a methyltransferase reaction. The location of the "hot spot" residue is at the cytoplasmic surface of the plasma membrane, and it is thus located at or near the head groups of membrane phospholipids, raising the possibility that the S-adenosylated form of the $D_4$ receptor might serve as a donor of methyl groups for methylation of the phospholipid phosphatidylethanolamine (PE) in the stepwise synthesis of phosphatidylcholine (PC).

Phosphatidylethanolamine (PE) is sequentially N-methylated by the action of two enzymes, phospholipid methyltransferases I and II (PLMT I and II), located on the inner and outer sides of the plasma membrane respectively (Hirata et al., Science 209:1082, 1980). Formation of N-monomethyl PE by PLMT I has been linked to the control of the membrane microviscosity, with increased formation leading to decreased microviscosity (i.e., increased membrane fluidity). To determine whether $D_4$ receptors might play a role in phospholipid methylation, CHO cells transfected with human $D_4$ receptor were incubated with [$^3$H]-methyl-methionine for 1 hr. in the presence or absence of dopaminergic ligands and GTP, followed by extraction of phospholipids and determination of [$^3$H] incorporation. The basal level of phospholipid methylation, however, could be augmented by about 30% by addition of a combination of GTP (1 mM) and dopamine (10 μM). The inclusion of the dopamine antagonists haloperidol (1 μM) (or clozapine) produced a decrease in phospholipid methylation to a level which was approximately 75% below the original basal level. In studies with PC12 cells, haloperidol treatment caused a similar decrease in phospholipid methylation, suggesting that dopamine receptor-dependent phospholipid methylation may be a feature of a number of cell types, including neuronal tissues.

An impairment in methylation reactions has previously been suggested to accompany and to cause schizophrenia. In an early hypothesis ("the transmethylation hypothesis"), a defect resulting in the formation of hallucinogens was proposed. Later, the "one-carbon hypothesis" suggested a defect in biochemical pathways involving methionine, S-adenosylmethionine and folic acid. To determine whether $D_4$ receptor-dependent phospholipid methylation was altered in individuals with schizophrenia, males ages 27–70 with well documented schizophrenia by DSM-IV criteria, were studied and compared with normal controls. Lymphocytes were incubated for 1 hr. in [$^3$H] methionine in the presence and absence of a combination of dopamine (10 μM) and GTP (1 μM) with and without haloperidol (1 μM). Basal phospholipid methylation was approximately 3.5-fold lower in the patient samples, indicating a profound defect in this pathway. Dopamine/GTP stimulated methylation by an average of 30% in controls and by 165% in patients. Haloperidol inhibition reached 25% below basal in controls and 39% below basal in patients. The results confirm the presence of a defect in one-carbon metabolism in schizophrenia and show that this defect is remarkably prominent in the phospholipid methylation pathway involving the dopamine $D_4$ receptor. Consequently, an altered membrane fluidity, in the composition of cell membranes such as nerve membranes, appears to play a significant role in producing the symptoms of schizophrenia.

Figure 2:
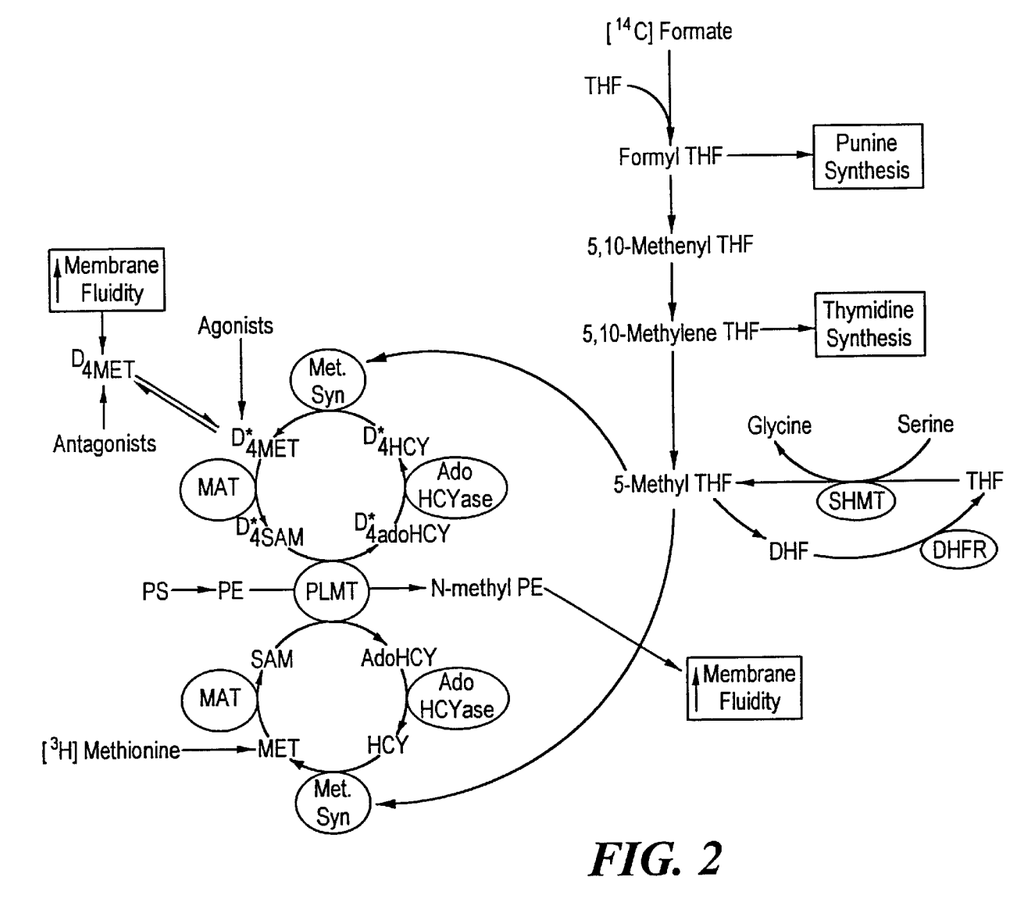
FIG. 2 is a schematic outline of metabolic pathways showing the use of [$^{14}$C] formic acid or [$^3$H] methionine to measure $D_4$ receptor-dependent and receptor-independent phospholipid methylation.

By placing these observations in the context of those made in earlier investigations of methionine metabolism, it is possible to formulate a unified "phospholipid methylation hypothesis" which combines the dopamine hypothesis of schizophrenia with the previously postulated theories of a defect in single carbon metabolism. Referring to FIG. 2, PLMT I-mediated N-methylation of PE is the initial step in phospholipid methylation. The $D_4*_{SAM}$ form of dopamine $D_4$ receptors can now be recognized to play a significant role as a source of methyl groups for this reaction while SAM itself presumably provides the additional receptor-independent source. As shown in the lower portion of the figure, the classical methionine cycle provides for methyl donation to phospholipid methyltransferase I (PLMT I) by formation of S-adenosylmethionine via the action of methionine adenosyltransferase (MAT). After methyl transfer, adenosylhomocysteine hydrolase (Ado Hcyase) removes the adenosyl moiety from adenosylhomocysteine and methionine is reformed via the action of methionine synthase (Met Synthase) to complete the cycle. Methionine synthase utilizes cobalamin (Vit $B_{12}$) to effect the methylation of homocysteine, with 5-methyl tetrahydrofolate (5-methyl THF) serving as the primary methyl donor. Serine hydroxymethyltransferase (Serine HMT) forms 5,10-methylene THF from the conversion of serine to glycine. The active R* form of the dopamine $D_4$ receptor ($D_4*_{MET}$) is adenosylated at M313 by MAT to yield $D_4*_{SAM}$ which can serve as a donor of methyl groups for N-methylation of PE by PLMT I. The remainder of the $D_4$ cycle is hypothesized to involve the actions of AdoHcyase and Met Synthase. Binding of negative antagonists to the inactive $D_4$ state of the receptor can serve to reduce its participation in phospholipid methylation. As a transmembrane protein, the $D_4$ receptor may be conformationally sensitive to changes in membrane fluidity, creating the potential for negative feedback regulation.

Clearly the net amount of PE methylation will depend upon three factors: 1) the concentration of the substrate PE; 2) availability of the methyl donors SAM and $D_4*_{SAM}$; and 3) the catalytic activity provided by PLMT I. Availability of $D_4*_{SAM}$ is dependent upon a number of factors including the density of $D_4$ receptors and the prevailing level of the $D_4*_{MET}$ state. Both SAM and $D_4*_{SAM}$ are dependent upon MAT activity and the efficiency of those events which allow for restoration of the methionine form of the receptor after methyl donation, some of which are outlined in FIG. 2. In short, the dynamics of the methionine cycle of methyl donation determine the ability of both SAM and the $D_4$ receptor to supply methyl groups for phospholipid methylation.

The following examples are presented to illustrate the advantages of the present invention and to assist one of ordinary skill in making and using the same. These examples are not intended in any way otherwise to limit the scope of the disclosure.

EXAMPLE I

Involvement of a $D_4$ Dopamine Receptor in Phospholipid Methylation

Figure 3A:
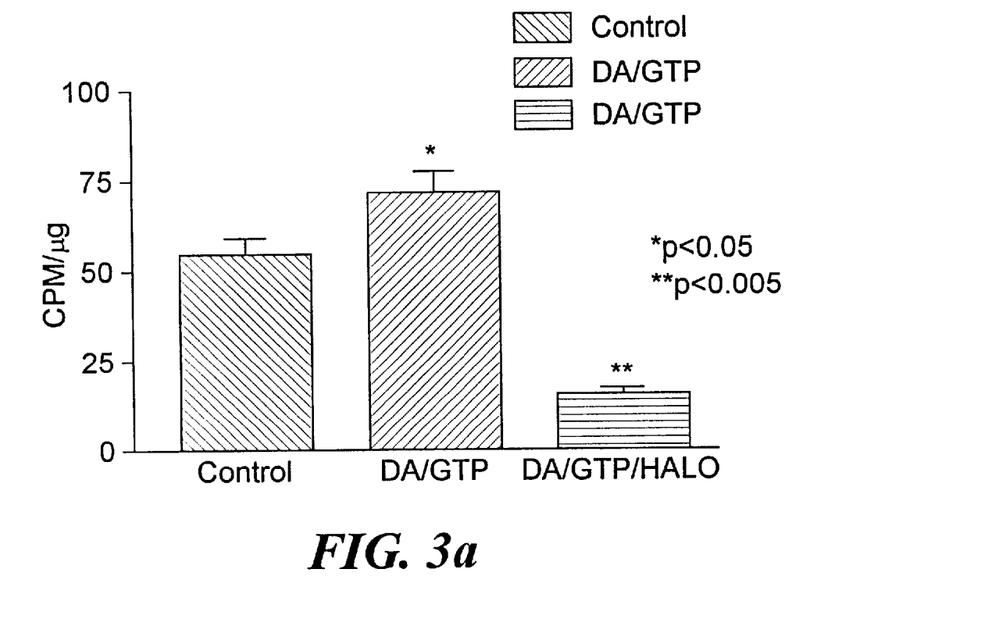
FIGS. 3a, 3b and 3c show involvement of $D_4$ dopamine receptor in phospholipid methylation.
Figure 3B:
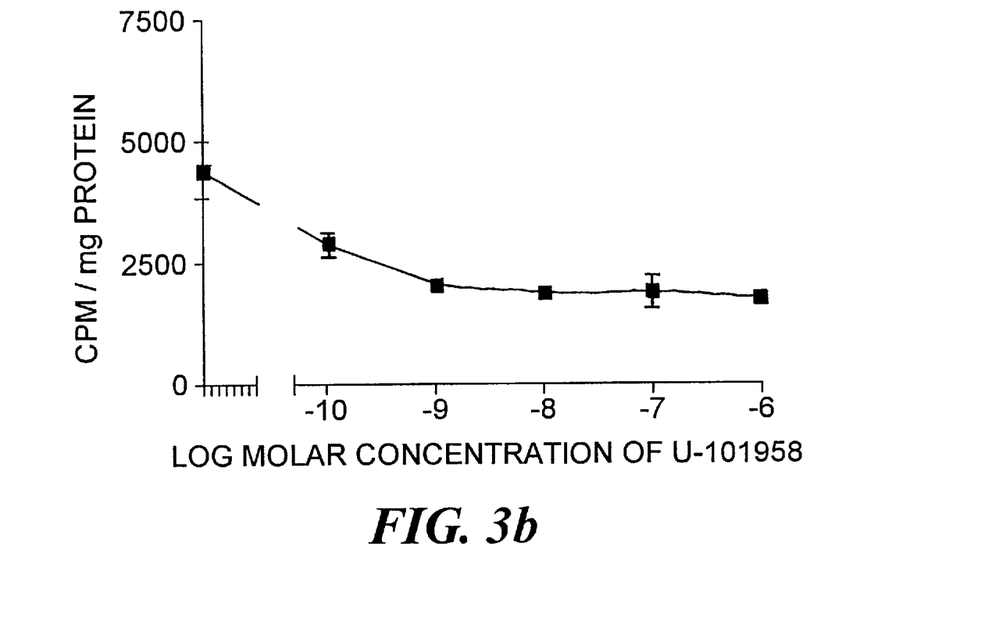
Figure 3C:
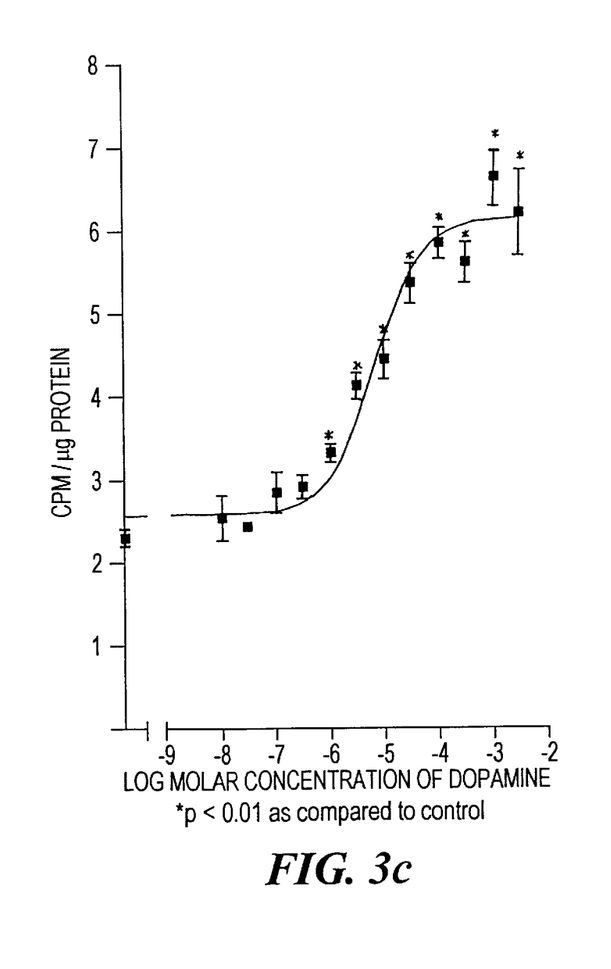

Incorporation of [$^3$H] label into phospholipids was measured in intact CHO cells transfected with the $D_4$ receptor gene (CHO/$D_4$ cells) after incubation with [$^3$H-methyl] methionine. The media of cells growing in monolayer was changed to 1 ml of Hank's balanced salt solution, nucleoside free, containing 8 μCi/ml [$^3$H-methyl] methionine. After a 60 min incubation, 1.5 ml of ice-cold 10% trichloroacetic acid (TCA) was added, and cells were harvested and centrifuged. The pellet was washed with 2.5 ml of TCA and extracted with 15 ml of a 6:3:1 mixture of $CHCl_3/CH_3OH/$ HCl (2 M). The CHCl$_3$ phase was washed twice with 4 ml of 0.1 M KCl in 50% CH$_3$OH, and an aliquot of the phospholipid-containing CHCl$_3$ was dried and counted. The graph depicted in FIG. 3a shows cells treated with either vehicle (Control), the D$_4$ receptor-selective agonists GTP (1 mM) and dopamine (10 μM) (DA/GTP) or both GTP and dopamine plus the D$_4$ receptor-selective antagonist haloperidol (1 μM) (HALO) at the start of [$^3$H-methyl]methionine incubation. A small stimulation of phospholipid methylation by the agonists GTP and dopamine and a large inhibition when the antagonist haloperidol is simultaneously included was observed. FIG. 3b shows dose-dependent inhibition of [$^{14}$C] formate-labelled phospholipid methylation in CHO/D$_4$ cells grown in nucleoside-free medium by the highly D$_4$-selective antagonist U-101,958. FIG. 3c shows dose-dependent dopamine stimulation of [14C] formate-labelled phospholipid methylation in SK-N-MC cells, which are derived from a human neuroblastoma and naturally contain the D$_4$ receptor, grown in the presence of nucleosides.

Referring again to FIG. 3b, dose-response studies in CHO cells with the D$_4$ receptor-selective antagonist U-101,958 conducted in the absence of agonist indicated that its inhibitory effects occurred at concentrations consistent with occupation of dopamine D$_4$ receptors, with an IC$_{50}$ of 0.2 nM as compared to its reported K$_D$ of 1 nM (Schlacter et al., Soc. Neurosci. Abstr. 21:252.7, 1995). Similar results were obtained with another D$_4$-selective antagonist L-745,870. This inhibition verifies that spontaneous activity of the D$_4$ receptor does indeed play an important role in phospholipid methylation, especially under nucleoside free growth conditions. The magnitude of antagonist effects suggest that the D$_4$ receptor can serve as a significant source of methyl groups, supplemented by a dopamine antagonist-insensitive component which likely represents the contribution of S-adenosyl methionine itself.

EXAMPLE II

Figure 4A:
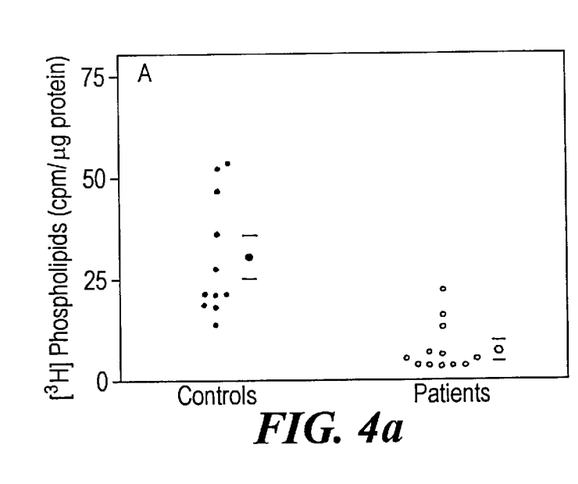
FIGS. 4a and 4b show phospholipid methylation in lymphocytes from persons with schizophrenia vs. normal controls.
Figure 4B:
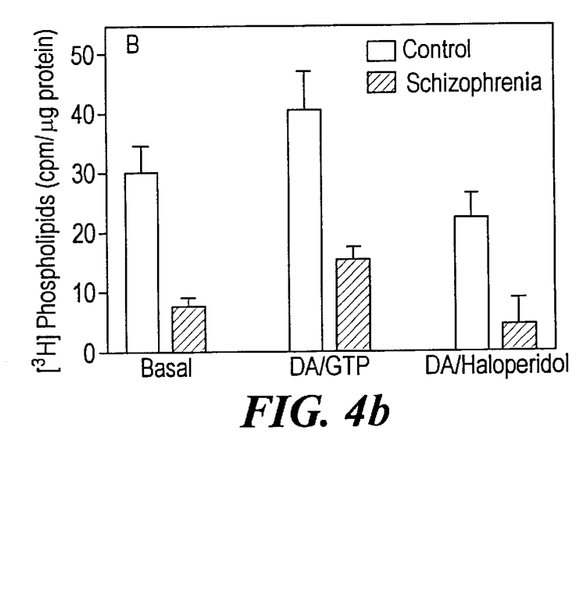

Phospholipid Methylation in Lymphocytes from Persons with Schizophrenia vs. Normal Controls To determine whether D$_4$ receptor-dependent phospholipid methylation was altered in schizophrenia, the labelling of phospholipids by [$^3$H] -methyl-methionine in lymphocytes obtained from people with schizophrenia (as defined by DSM IV diagnostic criteria *Diagnostic and Statistical Manual of Mental Disorders* (4th Edition), American Psychiatric Association, Washington, D.C., 1987, pp. 759–764) under medical treatment) was measured as compared to lymphocytes from healthy controls. Lymphocytes were isolated as previously described (De La Rosa et al., J. Biol. Chem. 267:10699, 1992) and aliquots of 4×10$^6$ cells were resuspended in Hank's balanced salt solution containing 8 μCi/ml [$^3$H-methyl]methionine for 60 min. Dopamine (10 μM) and GTP (1 mM) with or without haloperidol (1 μM) were added to additional groups. Incorporation of [$^3$H-methyl] label into phospholipids was determined as described in Example I. (A) Individual basal levels of phospholipid methylation and their mean =/- SEM. (B) Influence of dopamine/GTP and haloperidol on phospholipid methylation in control and schizophrenia samples. Differences between control and patient values are significant (p<0.001) for all treatment groups. The mean basal level of phospholipid methylation in patient samples was less than one-third the value of controls, indicating a major deficit in this process (FIG. 4A). In both groups, the addition of dopamine and GTP caused a significant increase in methyl incorporation while haloperidol caused a significant decrease (FIG. 4B), but the percentage changes in control were less than had been observed in CHO cells. However, these effects were relatively exaggerated in patient lymphocytes, associated with their low initial values. The difference between the agonist-stimulated and antagonist-inhibited values, which can be considered as the potential contribution dopamine receptors can make to this process, was only 20% smaller in the schizophrenia group. Thus while D$_4$ dopamine receptors are important in determining the level of phospholipid methylation in isolated lymphocytes, especially in individuals with schizophrenia, the large deficiency in schizophrenia appears to involve aspects other than the receptor contribution per se.

MATERIALS AND METHODS

Materials. U-101,958 maleate and L-745,870 hydrochloride, two examples of D$_4$ receptor-selective antagonists, were purchased from Research Biochemicals International (Natick, Mass.). [$^{14}$C]-formic acid was obtained from American Radiolabeled Chemicals Inc. (St. Louis, Mo.).

Cell Preparations. CHO cells transfected with the D$_4$ receptor gene were fed with minimum essential medium (alpha modifications, with or without nucleosides) (pH 7.2) containing 2mM L-glutamine, W/G418 antibiotic (400 mg/L), donor horse serum (2.5%), fetal bovine serum (2.5%), penicillin/streptomycin/fungizone (1%) , CuSO$_4$ (10$^{-6}$M). Cells (200,000 cells/well) were plated in 6-well-plates and placed in 5% CO$_2$ incubator at 37° C.

Phospholid Methylation Assay. Two-day-old confluent, cultured D$_4$-transfected CHO cells were used for assay. The pH of Hank's balanced buffer (HBSS) was adjusted to pH 7.4 using sodium bicarbonate buffer. [$^4$C]-formic acid (1 μCi/ml) and pharmacological agents were added to HBSS. Feeding medium was removed from the well and then 600 μl of the HBSS solution with the radiolabelled formic acid (warmed to 37° C.) was added to each well of 6-well-plates. Plates were incubated at 37° C. for 30 minutes in the culture incubator. The reaction was stopped by washing once with ice-cold PBS (pH 7.4) and, after aspirating off the HBSS, 500 μl of 10% trichloroacetic acid (TCA) was added. Cells were harvested by scraping with a cell scraper and transferred into a plastic microcentrifuge tube. Another 500 μl of TCA was added to rinse and transferred into the same tube. A sample (100 μl) was taken out for Lowry protein assay after the cells were homogenized. Each tube was spun in a bench top minifuge at 12,000 rpm for 15 minutes. After the TCA supernatant was aspirated off, 2N HCl (150 μl) and 100% methanol (450 μl) were added to each tube. The pellets were homogenized and 900 μl of chloroform (CHCl$_3$) was added to each tube. The sample tubes were placed on a shaker for 1 hour at room temperature to allow for phase separation and the top aqueous layer was removed by aspiration after shaking. 0.1 M KCl in 50% methanol (500 μl) was then added and the top aqueous layer was carefully removed by aspiration after thorough vortexing. The CHCl$_3$ layer was saved for scintillation counting. 300 μl of the CHCl$_3$ layer was transferred to a counting vial and evaporated to dryness by a heated water bath. Six replicate values were obtained for each experimental group. CPM values were normalized to the protein content of each sample and expressed as the mean +/- S.E.M. for the group. Differences between groups were analyzed by a t-test with p<0.05 as the criterion for significance.

Use

The metabolic relationships described herein have been used to develop methods of identifying therapeutic processes or agents for treating schizophrenia or a related neuropsychiatric disorder. These screening methods include establishing a cultured cell line, either naturally expressing $D_4$ receptor or transfected with the $D_4$ receptor gene, as an assay system; making an initial determination of the level of phospholipid methylation in the cultured cells; administering the candidate therapeutic process or agent to be assessed to the cultured cell assay system; and determining the level of phospholipid methylation following introduction of the candidate process or agent. An increase in the level of phospholipid methylation subsequent to administration of the candidate therapeutic process or agent indicates that the candidate process or agent is potentially therapeutically effective for treating schizophrenia or a related neuropsychiatric disorder. The particular influence of the candidate therapeutic process or agent on $D_4$ receptor-dependent phospholipid methylation is assessed by a comparison of agonist stimulated VS. antagonist-inhibited methylation levels. An increase in the receptor component indicates a potentially useful effect on dopamine function in the brain.

A similar method can be used to assess the effectiveness of the therapeutic process or agent for treating schizophrenia or a related neuropsychiatric disorder in a patient.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by definitions contained in the appended claims and equivalents thereof.

What is claimed is:

1. A method for assisting in the diagnosis of schizophrenia or depression in an individual, comprising the steps of:

(a) determining the level of phospholipid methylation in a viable tissue sample from an individual to be tested, wherein the level of phospholipid methylation is determined by labelling of the methylfolate pool;

(b) determining the level of $D_4$ receptor contribution to said phospholipid methylation in said tissue sample;

(c) comparing the level of phospholipid methylation determined in step (a) with the level of phospholipid methylation in a viable tissue sample from a normal individual, wherein a lower level of phospholipid methylation in the tissue sample from the individual to be tested when compared to that in the tissue sample from the normal individual is indicative of schizophrenia or depression in the tested individual; and (d) comparing the level of $D_4$ receptor contribution to said phospholipid methylation determined in step (b) with the level of $D_4$ receptor contribution to said phospholipid methylation in said tissue sample from said normal individual, wherein a lower level of $D_4$ receptor contribution to said phospholipid methylation in the tissue sample from the individual to be tested than in the tissue sample from the normal individual is further indicative of schizophrenia or depression in the tested individual.

2. The method of claim 1, wherein the level of phospholipid methylation is determined by labelling the methylfolate pool with [$^{14}$C]-formic acid.

3. The method of claim 1, wherein the tissue sample is a blood cell sample.

4. The method of claim 1, wherein the tissue sample is a lymphocyte.

* * * * *